United States Patent [19]
Hsu et al.

[11] Patent Number: 6,004,560
[45] Date of Patent: Dec. 21, 1999

[54] NASAL SPRAY (DROP) FOR TREATING FEVER/COLD, AND ITS PREPARATION

[76] Inventors: Wu-Ching Hsu; Su- Hsien Keng, both of No 2, Alley 16, Lane 41, Sec 2, Nan-Ching E. RD., Taipei, Taiwan

[21] Appl. No.: 09/192,289

[22] Filed: Nov. 16, 1998

[51] Int. Cl.⁶ .................................................. A01N 65/00
[52] U.S. Cl. ........................................................... 424/195.1
[58] Field of Search .......................................... 424/195.1

[56] References Cited

PUBLICATIONS

Derwent Computer Abstract DRUGU 85–06771 Adachi et al "Effects of Hot Water Extracts of Several Kanpo–Prescriptions on Macrophage Procoagulant Activity.I" J. Pharm. Soc. Jap 104 No. 9, pp. 959–65 (1984).

*Primary Examiner*—Herbert J. Lilling
*Attorney, Agent, or Firm*—Bacon & Thomas

[57] ABSTRACT

A nasal spray (drop) for treating fever/cold, and its preparation. The nasal spray (drop) is made by: obtaining a liquid by boiling Bupleurum Scorzonerifolium Willd, Radix Lastidis Lndigotica and Folium Lastidis for a long time in water, and then mixing the liquid thus obtained with Vitamin C. The nasal spray (drop) can be directly applied to the nasal cavity, and absorbed by the nasal mucosa to clear heat and sore, to release influenza symptoms such as head ache, stuff nose, coughing, sore throat, sneezing, nose-dropping and whole-body pain, and to treat fever due to infection of upper respiratory tract.

22 Claims, 6 Drawing Sheets

Fig. 1

| Group | Dosage (g/kg) | Number of animal tested | Basic body temperature | Before applying | After applying | | | |
|---|---|---|---|---|---|---|---|---|
| | | | | | 0.5h | 1h | 2h | 4h |
| Blank reference group | — | 10 | 37.9 ± 0.34 | 39.2 ± 0.46 | 39.3 ± 0.45 | 39.2 ± 0.44 | 39.2 ± 0.41 | 39.1 ± 0.48 |
| Tylenol P.O. Liquid group | 0.14 | 10 | 37.8 ± 0.38 | 39.2 ± 0.41 | 38.7 ± 0.45 ** | 38.4 ± 0.49 ** | 38.4 ± 0.46 ** | 38.5 ± 0.48 ** |
| Analgin group | 0.08 | 10 | 37.9 ± 0.37 | 39.2 ± 0.32 | 39.0 ± 0.36 | 38.8 ± 0.44 | 38.8 ± 0.42 * | 38.8 ± 0.44 |
| 9606 Nasal spray (drop) group | 1.2 | 10 | 37.9 ± 0.36 | 39.3 ± 0.37 | 38.9 ± 0.42 | 38.8 ± 0.40 * | 38.6 ± 0.43 * | 38.6 ± 0.49 * |
| 9606 Nasal spray (drop) group | 2.4 | 10 | 37.8 ± 0.36 | 39.2 ± 0.38 | 38.7 ± 0.41 ** | 38.6 ± 0.39 ** | 38.5 ± 0.41 ** | 38.4 ± 0.44 ** |

| DATE 1996 | NAME | AGE | DIAGNOSIS | DOSAGE (DROPS) | BEFORE APPLYING TEMPERATURE | BEFORE APPLYING SYMPTOMS | TEMPERATURE (°C) AFTER APPLYING 5' | 10' | 30' | 60' | SYMPTOMS AFTER APPLYING |
|---|---|---|---|---|---|---|---|---|---|---|---|
| 2.10 | Chiang Yang-Yang | 8 | Fever | 10 | 40.3 | Sore Throat, Coughing | 39.9 | 39.2 | 38.4 | 37.6 | Stuffy-nose disappear, Coughing better |
| 2.15 | Liu Yu-Yang | 9 | Infection of Upper Respiratory Tract | 8 | 38.5 | Sneezing, Tonsilitis | 38.2 | 37.6 | 36.2 | 36.8 | Disappear |
| 2.16 | Chang Yang | 2 | Infection of Respiratory Tract | 8 | 39.1 | Sore Throat | 38.4 | 38.2 | 38.4 | 37.5 | Better |
| 2.18 | Han Yueh | 1 2/12 | Infection of Respiratory Tract | 4 | 39.4 | Sore Throat, Coughing | 38.6 | 38 | 38 | 37.1 | Relief of Coughing & Sore-throat |
| 2.20 | Jen Chi-Hui | 1 3/12 | Infection of Respiratory Tract | 4 | 38.2 | Sneezing, Tonsilitis | 38.2 | 38.6 | 37.2 | 36.5 | Better |
| 2.21 | Ho Chi-Hui | 7/12 | Infection of Respiratory Tract | 2 | 39.2 | Fever, Headache | 38.7 | 39 | 38.2 | 37 | Better |
| 2.22 | Ho Chi-Hui | 7/12 | Diarrhea | 2 | 39³ | Fever, Diarrhea | 38.5 | 36.2 | 36.5 | 36.5 | Better |
| 2.25 | Chai King-Hui | 7/12 | Pneumonia | 4 | 38⁷ | Fever, Stuffy Nose | 39.1 | 38.8 | 38.3 | 36.7 | Better |
| 2.27 | Kao Yang | 4 | Diarrhea | 4 | 39² | Diarrhea, Fever, Celialgia | 39.1 | 38.7 | 38.7 | 36.8 | Better, lower temperature |
| 3.01 | Wei Meng-Yuan | 6 | Pneumonia | 8 | 39⁴ | Sore Throat, Fever, Coughing | 38.5 | 38.7 | 38 | 36.8 | Lower temperature, better |
| 3.03 | Chang Shih-Chieh | 6 | Infection of Respiratory Tract | 4 | 38⁵ | Sore Throat, Fever, Coughing | 39.3 | 38.5 | 37.9 | 37.5 | The same |
| 3.05 | Chang Shih-Chieh | 1 10/12 | Infection of Respiratory Tract | 6 | 37⁶ | Sore Throat, Fever, Coughing | 39.2 | 38.1 | 37.6 | 36.5 | Better |
| 3.06 | Sun Che-Wen | 3 6/12 | Infection of Respiratory Tract | 6 | 39⁶ | Fever, Coughing | 39.1 | 38.4 | 37.8 | 36.4 | Better |
| 3.08 | Tung Che-Yuan | 4 | Infection of Respiratory Tract | 4 | 39⁸ | Fever, Coughing | 38.5 | 37.6 | 36.8 | 36.4 | No obvious change |
| 6.06 | Lu Lei | 8 | Infection of Respiratory Tract | 4 | 39² | Fever, Discomfortable | 39 | 38.5 | 38.2 | 37.1 | Better, lower temperature |
| 6.30 | Chou Yen | 6 | Infection of Respiratory Tract | 2 | 39 | Headache, Discomfortable | 37.5 | 37.1 | 36.8 | 36.2 | Disappear |
| 7.02 | Shin | 5 | Infection of Respiratory Tract | 2 | 38² | Headache, Coughing | 38.8 | 38.2 | 37.1 | 36.9 | Better |
| 7.18 | Yu-Jen Hsia Li | 2 | Infection of Respiratory Tract | 4 | 39 | Coughing, Coughing | 38.8 | 38.4 | 37.4 | 36.5 | Better, lower temperature |
| 8.06 | Chen Hsiao-Wen | 1 6/12 | Infection of Respiratory Tract | 4 | 39² | Coughing, Coughing | 39.2 | 38.4 | 37.1 | 36.8 | Better, lower temperature |

Fig. 3

| DATE 1996 | NAME | AGE | DIAGNOSIS | DOSAGE (DROPS) | BEFORE APPLYING | | TEMPERATURE AFTER APPLYING (°C) | | | | SYMPTOMS AFTER APPLYING |
|---|---|---|---|---|---|---|---|---|---|---|---|
| | | | | | TEMPER-ATURE | SYMPTOMS | 5' | 10' | 30' | 60' | |
| 1.5 | Chang Kuan-Shing | 3 4/12 | Infection of Upper Respiratory Tract | 8 | $39^4$ | Sore Throat, Whole-body Pain | 39 | $38^5$ | $37^2$ | $36^6$ | Better |
| 1.6 | Lee Kang | 4 6/12 | Diarrhea | 8 | 39 | Stuffy Nose, Sore Throat, | $39^2$ | $38^1$ | $37^3$ | $36^5$ | The same |
| 1.6 | Lee Hsueh | 3 4/12 | Infection of Upper Respiratory Tract | 8 | $39^1$ | Stuffy Nose, Sore Throat, Whole-body Pain | $38^7$ | $37^2$ | $36^5$ | $36^4$ | Stuffy-nose Disappear, pains relief |
| 1.7 | Wang Shih | 6 | Fever | 10 | $39^6$ | Headache, Stuffy Nose, Coughing | $39^2$ | $38^7$ | $36^2$ | $36^5$ | Stuffy-nose Disappear, Coughing better |
| 1.9 | Lu Chao-Han | 5 6/12 | Infection of Upper Respiratory Tract | 10 | $38^9$ | Stuffy Nose, Coughing | 37 | $36^4$ | $36^3$ | $36^4$ | Stuffy-nose Disappear, Coughing better |
| 1.9 | Lee Tsung-Tsung | 2 | Infection of Upper Respiratory Tract | 6 | $38^8$ | Stuffy Nose, Coughing | $38^2$ | $37^6$ | 37 | $36^6$ | Stuffy-nose Disappear, Coughing better |
| 1.10 | I Hung | 1 10/12 | Infection of Upper Respiratory Tract | 8 | $39^3$ | Stuffy Nose, Coughing, Headache | 39 | $38^2$ | 38 | $37^2$ | Stuffy-nose Disappear, Coughing better |
| 1.12 | Lee Hsiang-Yu | 1 4/12 | Infection of Upper Respiratory Tract | 4 | $38^7$ | Stuffy Nose, Sore Throat, | $38^5$ | $37^9$ | 36 | 36 | Disappear |
| 1.13 | Lo Su-Ching | 4 | Fever | 8 | $39^2$ | Stuffy Nose | 39 | $38^6$ | $37^9$ | $36^6$ | Disappear |
| 1.16 | Lee Ya-Nan | 6 | Fever | 10 | $39^4$ | Stuffy NOSE, Sore Throat | $39^2$ | $38^2$ | $38^1$ | $37^2$ | Disappear |
| 1.17 | Wang Hsiao-Hung | 3 4/12 | Infection of Upper Respiratory Tract | 8 | $38^5$ | Stuffy Nose, Sore Throat | 38 | $37^4$ | $36^5$ | $36^4$ | Disappear |
| 1.19 | Hsia Ching | 1 10/12 | Infection of Upper Respiratory Tract | 6 | $37^6$ | Stuffy NOSE, Sore Throat | $37^5$ | $37^2$ | 37 | $36^4$ | Disappear |
| 1.20 | Ten Yang | 3 6/12 | Infection of Upper Respiratory Tract | 8 | $39^6$ | Stuffy NOSE, Sore Throat, Pains | $39^1$ | $38^2$ | $37^6$ | $36^6$ | Better |
| 1.21 | Chong Yu-Hung | 4 | Fever | 10 | $39^6$ | Stuffy Nose, Coughing | 39 | $38^6$ | $38^6$ | $37^2$ | Better |
| 1.25 | Lee Hsiao-Yang | 6 | Fever | 10 | $39^2$ | Stuffy Nose, Coughing, Headache | $38^9$ | $36^2$ | $38^2$ | $37^1$ | Better |
| 1.26 | Liu Jen | 4 | Fever | 8 | $39^2$ | Stuffy Nose, Discomfortable | $38^2$ | $37^8$ | $36^2$ | $36^4$ | Better |
| 2.1 | King Hui | 5 | Fever | 10 | $38^2$ | Stuffy NOSE, Sore Throat | $37^5$ | $37^6$ | $36^4$ | $36^2$ | Stuffy-Nose Disappear |
| 2.5 | Nung Hsiao-Hua | 8 | Infection of Upper Respiratory Tract | 10 | 39 | Stuffy NOSE, Sore Throat | $38^2$ | $37^6$ | $37^9$ | $36^6$ | Stuffy-Nose Disappear |
| 2.6 | Sung Shuang | 5 4/12 | Infection of Upper Respiratory Tract | 8 | $39^2$ | Stuffy Nose, Headache | $39^1$ | $38^2$ | $36^4$ | $36^6$ | Stuffy-Nose Disappear, Headache relief |

Fig. 4

| DATE 1996 | NAME | AGE | DIAGNOSIS | DOSAGE (DROPS) | BEFORE APPLYING TEMPERATURE | BEFORE APPLYING SYMPTOMS | TEMPERATURE AFTER APPLYING (°C) 5' | 10' | 30' | 60' | SYMPTOMS AFTER APPLYING |
|---|---|---|---|---|---|---|---|---|---|---|---|
| 1.5 | Tsao Hun-Chung | 41 | Infection of Upper Respiratory Tract | 14 | $38^5$ | Headache, Discomfortable | $38^2$ | $37^8$ | $36^7$ | $36^7$ | Better |
| 1.8 | Liu Mei-Hwa | 48 | Infection of Upper Respiratory Tract | 14 | $39^1$ | Sore Throat, Coughing, Headache | $38^8$ | $38^6$ | $38^1$ | $37^1$ | Better |
| 1.9 | Lee Yu-Lin | 49 | Fever | 14 | $38^7$ | Stuffy Nose, Headache, Coughing | $38^5$ | $37^8$ | $36^9$ | $36^4$ | Stuffy-nose Disappear, other symptoms better |
| 1.10 | Wang Huan-Wen | 45 | Fever | 12 | $38^2$ | Stuffy Nose, Discomfortable | $38^6$ | $38^2$ | $37^4$ | $36^2$ | Stuffy-nose Disappear, other symptoms better |
| 1.12 | Yu Chen-Feng | 23 | Fever | 12 | $38^5$ | Stuffy Nose, Sore Throat, Sneezing | $38^2$ | $37^4$ | $36^8$ | $37$ | Stuffy-nose Disappear, other symptoms better |
| 1.20 | Wang Hsiao-Hwa | 74 | Fever | 18 | $38^6$ | Sore Throat, Sneezing, Discomfortable | $38^6$ | $37^9$ | $37$ | $36^8$ | Stuffy-nose Disappear, other symptoms better |
| 1.21 | Chiang Yen-Hung | 68 | Fever | 16 | $38^2$ | Sore Throat, Sneezing, Discomfortable | $37^8$ | $36^8$ | $36^4$ | $36^8$ | Stuffy-nose Disappear, other symptoms better |
| 1.23 | Lee Yu | 26 | Fever | 16 | $38^8$ | Sore Throat, Sneezing, Coughing | $38^4$ | $37^8$ | $36^8$ | $36^4$ | Stuffy-nose Disappear, coughing relief |
| 1.24 | Lo Su-Ching | 37 | Fever | 10 | $38^9$ | Sore Throat, Sneezing, Coughing | $38^8$ | $38^9$ | $37^2$ | $36^8$ | Stuffy-nose Disappear, sore-throat better |
| 2.3 | Chai Yu-Jung | 43 | Fever | 12 | $38^6$ | Stuffy Nose, Sore Throat, Seezing | $38^4$ | $38^5$ | $37^1$ | $37$ | Stuffy-nose Disappear, sore-throat better |
| 2.5 | Huang Hsiao-Hung | 28 | Fever | 12 | $38^4$ | Stuffy Nose, Sore Throat, Seezing | $38^2$ | $38$ | $37$ | $36^8$ | Stuffy-nose Disappear, sore-throat better |
| 2.7 | Fen Peng-Chen | 37 | Infection of Upper Respiratory Tract | 16 | $38^8$ | Stuffy Nose, Sore Throat, Coughing | $38$ | $37^2$ | $36^8$ | $36^5$ | Better |
| 2.8 | Huang Wen-Ping | 42 | Fever | 16 | $39^6$ | Stuffy Nose, Sore Throat, Coughing | $37^2$ | $37^8$ | $36^8$ | $36^2$ | Stuffy-nose Disappear, sore-throat better |
| 2.10 | Wong Yu-Fen | 50 | Infection of Upper Respiratory Tract | 16 | $38^4$ | Stuffy Nose, Sore Throat, Coughing | $38^1$ | $37^4$ | $36^8$ | $36^5$ | Better |
| 2.12 | Kung Fan-Chi | 47 | Fever | 16 | $37^9$ | Stuffy Nose, Headache, Coughing | $37^4$ | $36^8$ | $36^4$ | $36^2$ | Disappear |
| 2.14 | Huang Su-Ming | 35 | Infection of Upper Respiratory Tract | 16 | $38^6$ | Stuffy Nose, Headache, Coughing | $38^1$ | $36^2$ | $37$ | $37^5$ | Better |
| 2.16 | Chen Hsiao-Hung | 38 | Infection of Upper Respiratory Tract | 16 | $38^5$ | Stuffy Nose, Headache, Coughing | $38^8$ | $37^9$ | $38^2$ | $36^8$ | Stuffy-nose Disappear, sore-throat better |
| 2.18 | Lee Yu-Yuan | 41 | Fever | 12 | $39$ | Sore Throat, Coughing | $38^1$ | $37^4$ | $37$ | $36^8$ | Coughing is better, sore-throat disappear |
| 2.20 | Chang Hsueh-Feh | 45 | Fever | 16 | $38^8$ | Headache, Coughing | $37^4$ | $36^9$ | $36^3$ | $36^8$ | Coughing & headache better |

Fig. 5

| DATE 1996 | NAME | AGE | DIAGNOSIS | DOSAGE (DROPS) | BEFORE APPLYING | | TEMPERATURE AFTER APPLYING(°C) | | | | SYMPTOMS AFTER APPLYING |
|---|---|---|---|---|---|---|---|---|---|---|---|
| | | | | | TEMPER-ATURE | SYMPTOMS | 5' | 10' | 30' | 60' | |
| 2.20 | Chang Ming-Chun | 31 | Infection of Upper Respiratory Tract | 16 | $39^2$ | Headache, Discomfortable | $38^5$ | $37^9$ | $37^1$ | $36^8$ | Better |
| 2.22 | Niu Da-Wei | 58 | Infection of Upper Respiratory Tract | 16 | $38^8$ | Sore Throat, Coughing | $37^2$ | $38^4$ | $36^8$ | $36^4$ | Sore-throat & coughing better |
| 2.24 | Wang Hsiao-Li | 30 | Fever | 16 | $38^1$ | Discomfortable | $38$ | $37^5$ | $37^2$ | $36^8$ | Better |
| 4.7 | Liu Liu | 45 | Fever | 18 | $38^2$ | Discomfortable | $38$ | $37^2$ | $36^8$ | $36^5$ | Better, Obiously |
| 8.12 | Lee Hsiao-Niu | 23 | Fever | 20 | $39^6$ | Headache, Discomfortable | $39^2$ | $38^6$ | $38^6$ | $37^2$ | Better, Obiously |

Fig. 6

NASAL SPRAY (DROP) FOR TREATING FEVER/COLD, AND ITS PREPARATION

BACKGROUND OF THE INVENTION

The present invention relates to a nasal spray (drop) for treating fever/cold, and its preparation. The nasal spray (drop) is made by: obtaining a liquid by boiling Bupleurum Scorzonerifolium Willd, *Radix lastidis* Indigotica and *Folium lastidis* for a long time in water, and then mixing the liquid thus obtained with Vitamin C. The nasal spray (drop) can be directly applied to the nasal cavity, and absorbed by the nasal mucosa to clear heat and sore, to relieve influenza symptoms such as headache, stuff nose, coughing, sore throat, sneezing, runny nose and whole-body pain, and to treat fever due to infection of upper respiratory tract.

Most people see influenza (cold) as an insignificant disease. Actually, influenza (cold) is an acute infectious disease generally accompanied by a fever, stuff nose, headache, dry or sore throat. Many virus may cause influenza. Influenza virus are tiny, and can easily pass through the filter in the nasal passage into the inside of the body. The filter in the nasal passage can only catch virus of bigger size. Rapid multiplication of virus attacks nose and throat, causing influenza symptoms, and a complication such as pneumonia and bronchitis. Improper treatment of influenza may cause the patient to die. Influenza is indeed a common disease that cannot be ignored.

In Western medicine, it is recommended to take antibiotics for removing heat, cortisone for releasing stuff nose and antihistamine for freeing from influenza symptoms, as well to drink much water and to rest. Normally, Western medicine shows its effect rapidly. However, the use of Western medicine produces toxic chemical substance that is harmful to the internal organs of the body. Further, these chemical medicines are not satisfactory in use in releasing and preventing fever. Regular chemical influenza medicines are commonly made in capsules, tablets, suppositories, oral liquid, or spray (drop).

In Chinese medicine, influenza treating medicines are commonly symptom relieving medicines used to relieve symptoms indicating that the exterior of the human body has been attacked by exogenous harmful factors. Symptoms relieving medicines have effects in three ways, namely, (1) sweating the patient to relieve symptoms and expel external causes and to prevent external causes from affecting the internal organs of the body, (2) relaxing muscles to relieve symptoms from the muscles, and (3) letting out carbuncles. External causes include cold factors and febrile factors. Because symptoms may show the deficiency of vital energy of the patient, or indicate that the exterior of the human body or the internal organs have been affected, symptom relieving medicines include medicines to relieve symptoms caused by the cold factors, medicines to relieve symptoms caused by febrile factors, and medicines to relieve symptoms showing the deficiency of vital energy of the patient. Chinese medicines are safe in use, and produce little by-effect. They can be made in the form of a powder medicine and herb soup. However, Chinese medicines are inconvenient in use, and take much time to show the effect.

Chemical medicine and herbal medicine achieve certain effect in fever relieving and heat clearing. Physical temperature dropping methods include applying ice to the surface of the body, rubbing the skin with alcohol, washing away of bowels by injecting icy water, etc. These methods are clinically effective. However, in certain cases, the body temperature increases after the application of the aforesaid methods. The method of applying ice to the surface of the body and the method of rubbing the skin with alcohol are inconvenient to perform, further they cause the patient to feel severely chilly.

In general, the aforesaid conventional fever/cold treating measures by means of Western medicine, Chinese medicine, or physical treatment still have drawbacks.

SUMMARY OF THE INVENTION

It is the main object of the present invention to provide a nasal spray (drop) which can conveniently safety be applied to the patient to effectively treat fever/cold. It is another object of the present invention to provide a nasal spray (drop) for treating fever/cold which can be directly absorbed by nasal mucosa without being damaged by the function of liver, Ph value or enzyme of the stomach and intestine. The present invention provides a nasal spray (drop) for treating fever/cold. It is made by: obtaining a liquid by boiling Bupleurum Scorzonerifolium Willd, *Radix lastidis* Indigotica and *Folium lastidis* for a long time in water, and then mixing the liquid thus obtained with Vitamin C. When applied to the nasal cavity, the nasal spray (drop) is absorbed by the nasal mucosa to remove heat, to release sore and other influenza symptoms such as head ache, stuff nose, coughing, sore throat, sneezing, nose-dropping and whole-body pain, and to treat fever due to infection of upper respiratory tract. Effects of Bupleurum Scorzonerifolium Willd: reducing fever by reconciliation, relieving the depressed liver, soothing the liver and regulating the circulation of qi, invigorating vital function and elevating spleen yang. Indications of Bupleurum Scorzonerifolium Willd: alternate attacks of chills and fever, feeling of fullness and discomfort in the chest and hypochondrium, bitter taste and dry throat, headache and dizziness, stagnation of liver-qi, distending pain in the hypochondriac region, irregular menstruation, dysmenorrhea, proctoptosis, hysteroptosis, etc. Effects of *Radix lastidis* Indigotica: clearing away heat, detozicating, removing heat from the blood and relieving sore-throat. Indications of *Radix lastidis* Indigotica: affection by the exopathogenic wind-heat manifested as fever, headache, sore throat, mumps, suppurative infections on the body surface, blood-shot eyes, coma, hematemesis, epistaxis, craniofacial infection, etc. Effects of *Folium lastidis*: clearing away heat, detoxicating, removing pathogenic heat from blood and curing skin eruptions. Indications of *Folium lastidis*: headache, thirst, fever due to the exopathogenic wind-heat, high fever, unconsciousness, maculas due to the invasion of the blood by heat, and sore throat, jaundice, dysentery, carbuncle and cellulitis. Effects of Vitamin C: influenza preventing, improving body power of resistance, relieving influenza symptoms. Indications of Vitamin C: influenza caused by filtrable virus.

BRIEF DESCRIPTION OF THE DRAWINGS

FIGS. 3–6 are clinical survey charts showing the effects of the present invention.

DETAILED DESCRIPTION OF THE PREFERRED EMBODIMENT

Figure 1:
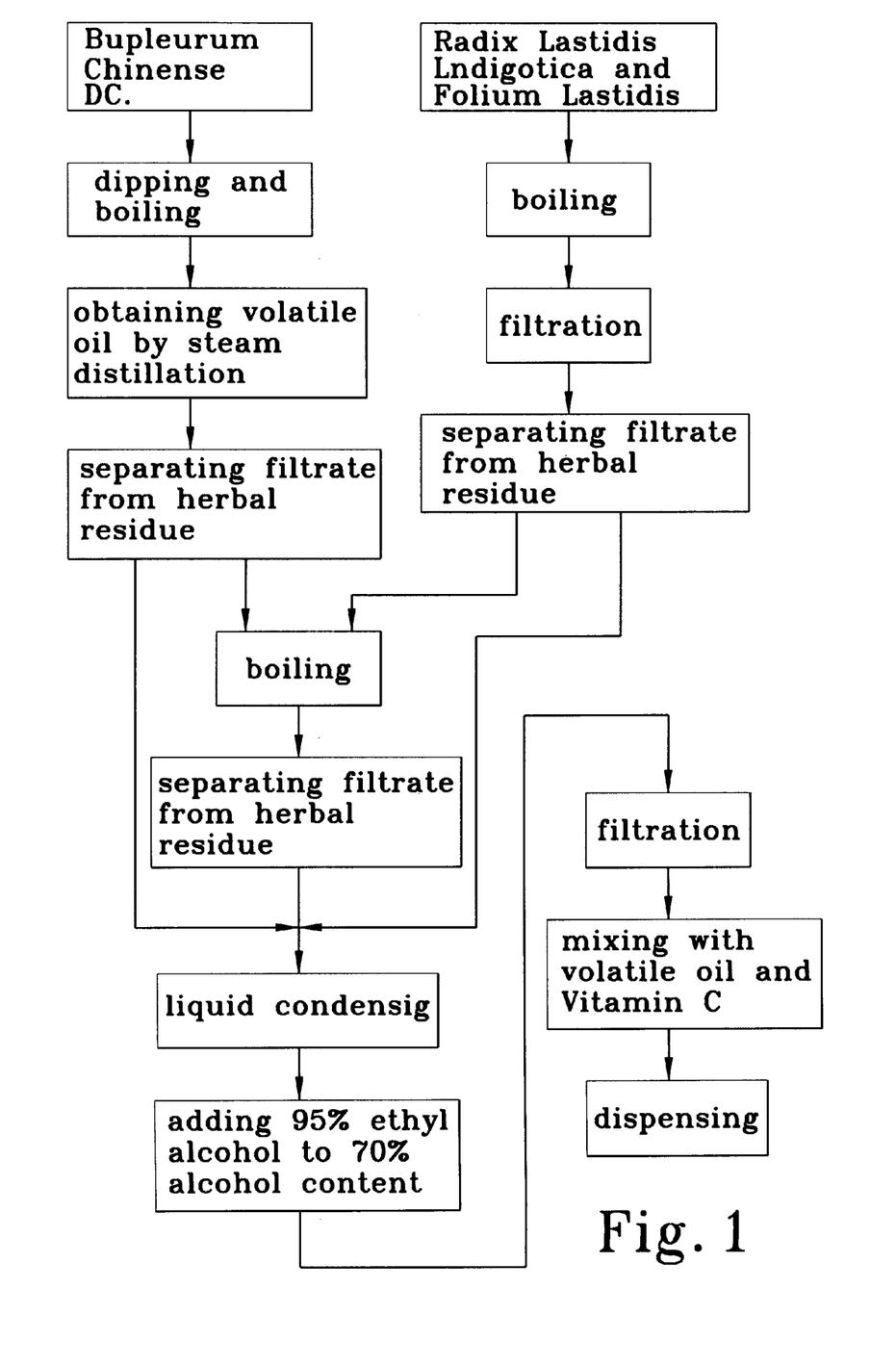
FIG. 1 is a flow chart showing the preparation of the pharmaceutical fever, cold, nose-dropping treating liquid according to the present invention.

Referring to FIG. 1, a nasal spray (drop) for treating fever/cold in accordance with the present invention comprises 250~300 g Bupleurum Scorzonerifolium Willd, 120~144 g *Radix lastidis* Indigotica, 120~144 g *Folium lastidis* and 10~12 g Vitamin C. When applied to the nasal cavity, the nasal spray (drop) is absorbed by the nasal mucosa to remove heat, to release sore and other influenza symptoms such as head ache, stuff nose, coughing, sore throat, sneezing, nose-dropping and whole-body pain, and to treat fever due to infection of upper respiratory tract.

The composition, effects, indications of the contents of the pharmaceutical fever, cold, runny nose treating liquid are outlined hereinafter:

1. Bupleurum Scorzonerifolium Willd
[Chemical Composition]

The root of Bupleurum Scorzonerifolium Willd contains a volatile oil, which contains β-terpinene, camphene, β-fenchene, isoborneol, β-terpincol, α-copaene, α-farnesene, aromadendrene, β-elemene, γ-muurolene, patchoulane, ledol, saikosaponin total 0.15% including saikosaponin a 0.05%, a minor amount of saikosaponin d and saikosaponin c 0.10%. The other part of Bupleurum Scorzonerifolium Willd above the earth (root) contains progesterone compound comprising quercetin, isoquercetin, isorhamnetin, rutin, narcissin.

[Pharmacology]

It is effective for painkilling. Experiments indicate satisfactory effect in painkilling. In an rate tail electric shock experiment, 478 mg/kg(1/4LD50) shows prominent effect of Bupleurum Scorzonerifolium Willd in painkilling. Hypodermic injection of 50 mg/kg or 100 mg/kg of saikosaponin A and syrup-like residue into the abdominal cavity of rate effectively inhibit rats from twisting. Syrup-like residue shows prominent effect in killing pain caused by external force. It is reported that saikosaponin can relax the muscles to relieve pain.

It is effective to inhibit coughing. Saikosaponin A has strong effect in inhibiting coughing. In a mechanical irritating experimentation, the coughing inhibiting effect of injecting 9.1 mg/kg saikosaponin coughing inhibiting ED50 into the abdominal cavity of a mouse is approximately equal to the effect of 7.6 mg/kg codeine phosphate. The coughing inhibiting effect of saikosaponin A has great concern with its dosage. The coughing inhibiting effect of saikosaponin A is most prominent when injecting 100~200 mg/kg to the abdominal cavity of the mouse.

[Effects and Indications]

Effects of Bupleurum Scorzonerifolium Willd: reducing fever by reconciliation, relieving the depressed liver, soothing the liver and regulating the circulation of qi, invigorating vital function and elevating spleen yang. Indications of Bupleurum Scorzonerifolium Willd: alternate attacks of chills and fever, feeling of fullness and discomfort in the chest and hypochondrium, bitter taste and dry throat, headache and dizziness, stagnation of liver-qi, distending pain in the hypochondriac region, irregular menstruation, dysmenorrhea, proctoptosis, hysteroptosis, etc.

2. *Radix lastidis* Indigotica
[Chemical Composition]

The root of *Radix lastidis* Indigotica contains indigotin, indigo, indirubin, β-sitosterol, γ-sitosterol, amino acids including arginine, glutamic acid, tyrosine, proline, valine and γ-aminobutyric acid, sinigri-n, indoxyl-β-glucoside, tryptanthrine, thiocyano-2-hydroxy-3-butene, epigoitrin, adenosine, palmitic acid, sucrose, and protein polysaccarides comprising 12% amino acid.

[Pharmacology]

It has anti-bacteria and anti-virus effects. In an in-vitro test, 100% *Radix lastidis* Indigotica boiled liquid is effective to inhibit Staphylococcus aureus, staphylococcus. In a *Radix lastidis* Indigotica injection anti-virus experiment using 50% TCID50 to infect single cell Vero-E6, 1:100 *Radix lastidis* Indigotica shows prominent virus killing effect. Extract of *Radix lastidis* Indigotica effectively inhibits multiplication of virus. Abdominal cavity injection of 25 mg/kg, 50 mg/kg, 100 mg/kg *Radix lastidis* Indigotica polyhexose enhances the reaction of rats against DNCB, endures the transformation of lymphatic cells, and improves the activity of NK cells of the spleen cells. Abdominal cavity injection of 50 mg/kg *Radix lastidis* Indigotica polyhexose greatly improve the immunity of rats. It shows the gaining of spleen weight, the increasing of total white cells and lymphatic cells. Furthermore, it enhances the formation of cells from antibodies.

[Effects and Indications]

Effects of *Radix lastidis* Indigotica: clearing away heat, detozicating, removing heat from the blood and relieving sore-throat. Indications of *Radix lastidis* Indigotica: affection by the exopathogenic wind-heat manifested as fever, headache, sore throat, mumps, suppurative infections on the body surface, blood-shot eyes, coma, hematemesis, epistaxis, craniofacial infection, etc.

3. *Folium lastidis*
[Chemical Composition]

The leaves of *Folium lastidis* contain indigo, indigotin, isatan B, indirubin, and inorganic elements including iron, titanium, manganese, zinc, copper, cobalt, nickel, selenium, chrome, arsenic. When dissolved in water, isatan B is turned into indigotin and D-xylo-5-hexulofuranosonic acid.

[Pharmacology]

It has anti-disease organism effect. Using a liquid obtained by boiling *Folium lastidis* in water in in-vitro tests shows a good effect in inhibiting *staphylococcus aureus, streptococcus, meningococcus, pneumococcus, typhoid bacillus, escherichia coli, diphtheria bacillus. Folium Lastidis* is also effective in inhibiting meningitis virus, mumps virus, influenza virus *Folium lastidis* is also effective in killing leptospira.

[Effects and Indications]

Effects of *Folium lastidis*: clearing away heat, detoxicating, removing pathogenic heat from blood and curing skin eruptions. Indications of *Folium lastidis*: headache, thirst, fever due to the exopathogenic wind-heat, high fever, unconsciousness, maculas due to the invasion of the blood by heat, and sore throat, jaundice, dysentery, carbuncle and cellulitis.

4. Vitamin C
[Chemical Composition]

Vitamin C contains mainly dextrose.

[Pharmacology]

Vitamin C is effective to prevent from catching cold. Symptoms of influenza include fever, cold, fatigue, severe coughing, sputum, stuffy nose, headache, joint pain, etc. An infection after influenza may cause pneumonia, bronchitis, tonsilitis, spinitis.

[Effects and indications]

Effects of Vitamin C: influenza preventing, improving body power of resistance, relieving influenza symptoms. Indication of Vitamin C: influenza caused by filtrable virus.

The preparation of the aforesaid nasal spray (drop) comprises the steps of:

1. dipping 250~300 g Bupleurum Scorzonerifolium Willd in equal volume of water for 2 hours, then boiling dipped Bupleurum Scorzonerifolium Willd in water at the ratio of one part of dipped Bupleurum Scorzonerifolium Willd with four parts of water and distilling the steam, so as to obtain 2 ml~2.4 ml volatile oil and 1000 ml~1200 ml filtrate, then receiving the volatile oil, the filtrate and the solid residue in separate containers;

2. boiling 120~144 g *Radix lastidis* Indigotica and 120~144 g *Folium lastidis* in water for one hour at the ratio of one part of *Radix lastidis* Indigotica and *Folium lastidis* with seven parts of water, then picking up the filtrate, and then receiving the filtrate thus obtained in a container;

3. mixing the residue of Bupleurum Scorzonerifolium Willd with the residue of *Radix lastidis* Indigotica and *Folium lastidis* into a mixture, then boiling the mixture in water for one hour at the ration of one part of the mixture with 5 parts of water, then picking up the filtrate, and then boiling the filtrate thus obtained in water for 40 minutes at the ratio of one part of the filtrate with four parts of water, and then picking up the filtrate;

4. mixing the first filtrate obtained from step 1, the second filtrate obtained from step 2 and the third filtrate obtained from step 3 into a mixture, and then condensing the mixture to a 1 ml liquid containing to 1 g raw medicine, then putting 95% ethyl alcohol to the liquid to reach 70% alcohol content;

5. standing the alcohol contained liquid at room temperature for 24 hours, then processing the liquid through a filtration process, enabling alcohol to be removed from the liquid to such an extent that 1 ml liquid contains 1 g raw medicine;

6. dissolving 10~12 g Vitamin C in 2 ml~2.4 ml volatile oil, then mixing dissolved volatile oil and Vitamin C mixture with the liquid obtained from step 5, then removing solid matter from the mixture so as to obtained finished nasal liquid, and then packing the finished nasal liquid in individual containers.

The nasal liquid medicine thus obtained is free from the effect Ph value or enzyme in entero, stomach and intestine, and can directly be absorbed by nasal mucosa. Therefore, the nasal liquid medicine will not be affected by the effect of liver function, and causes little toxic or side effect to the liver. In comparison with regular oral medicine, the nasal liquid medicine receives less interference and, achieves its medical effects quickly. It is quite convenient to apply the medicine to the nasal cavity of a child. In fever relieving and toxicoloy tests, the nasal spray (drop) of the present invention shows a satisfactory result. It is not only effective, but also safe in use. The fever relieving and toxicology experiments are outlined hereinafter:

A. Fever Relieving Effect of Nasal Spray (Drop)

[Test Samples]

1. Nasal spray (drop) containing raw medicine 2 g, clinical dosage for children 2 drops (about 0.1 ml) per every 10 kgs, dosage applied within 10 minutes, continuous dosage given for ten times, total amount of applied nasal spray (drop) about 0.2 g/kg. Nasal spray (drop) is diluted to the desired concentration before experiment.

2. Analgin injection, obtained from Wu-Han Pharmaceutical Plant, lot no. 951104, specifications 0.5 g/2 ml, clinical dosage for baby using 20% solution, each time 1~2 drops per each nostril, maximum dosage about 40 mg, average dosage 4 mg/kg. Analgin is diluted to the desired concentration before experiment.

3. Tylenol Children's P.O. liquid, obtained from Johnson American, lot no. SGM199, each vial 15 ml, every 0.8 ml containing 80 g acetaminophen, dosage given subject to patient's edge or body weight, average dosage about 0.12 ml/kg, i.e., 12 nl acetaminophen/kg.

4. Saline solution, obtained from Pin-Tin-Hsi Pharmaceutical Plant, Ho-Nan Province, P.R.C., lot no.9512301.

5. 10% mingling ferment liquid for fresh beer. Taking mingling ferment liquid for fresh beer, separating solid matter from mingling ferment liquid, washing the solid matter with saline repeatedly, then using 0.5% carboxymethyl cellulose to preparing a 10% concentration after a centrifugal process.

6. Wistar rats, weighing from 170 g to 210 g supplied by Animal Experimental Center of Ho-Nan Medical University.

[Method and Result]

Figure 2:
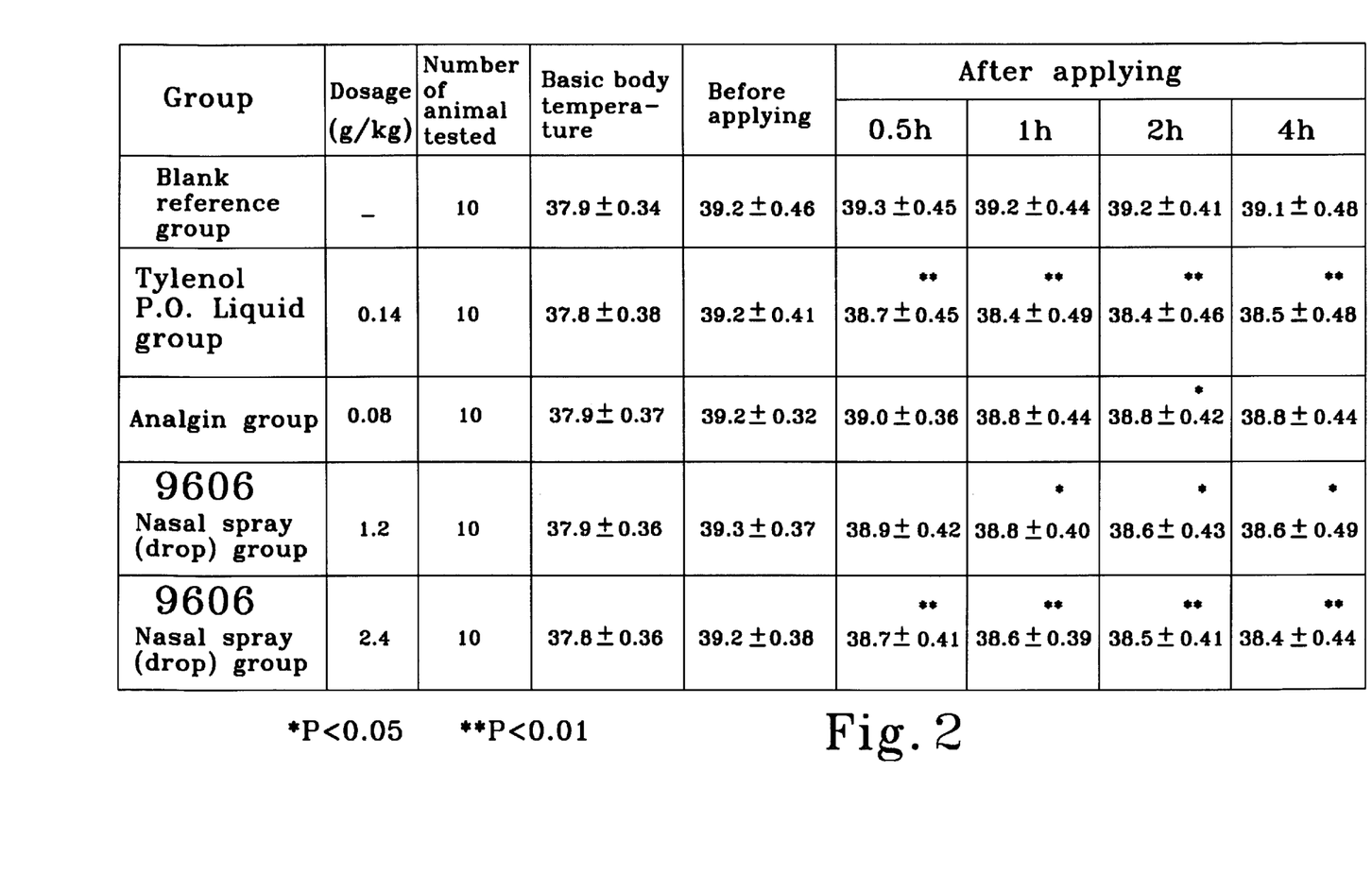
FIG. 2 is a comparison chart showing the temperature dropping effect between the present invention and conventional medicines on Wistar rats treated with mingling ferment liquid for fresh beer.
Figure 6:
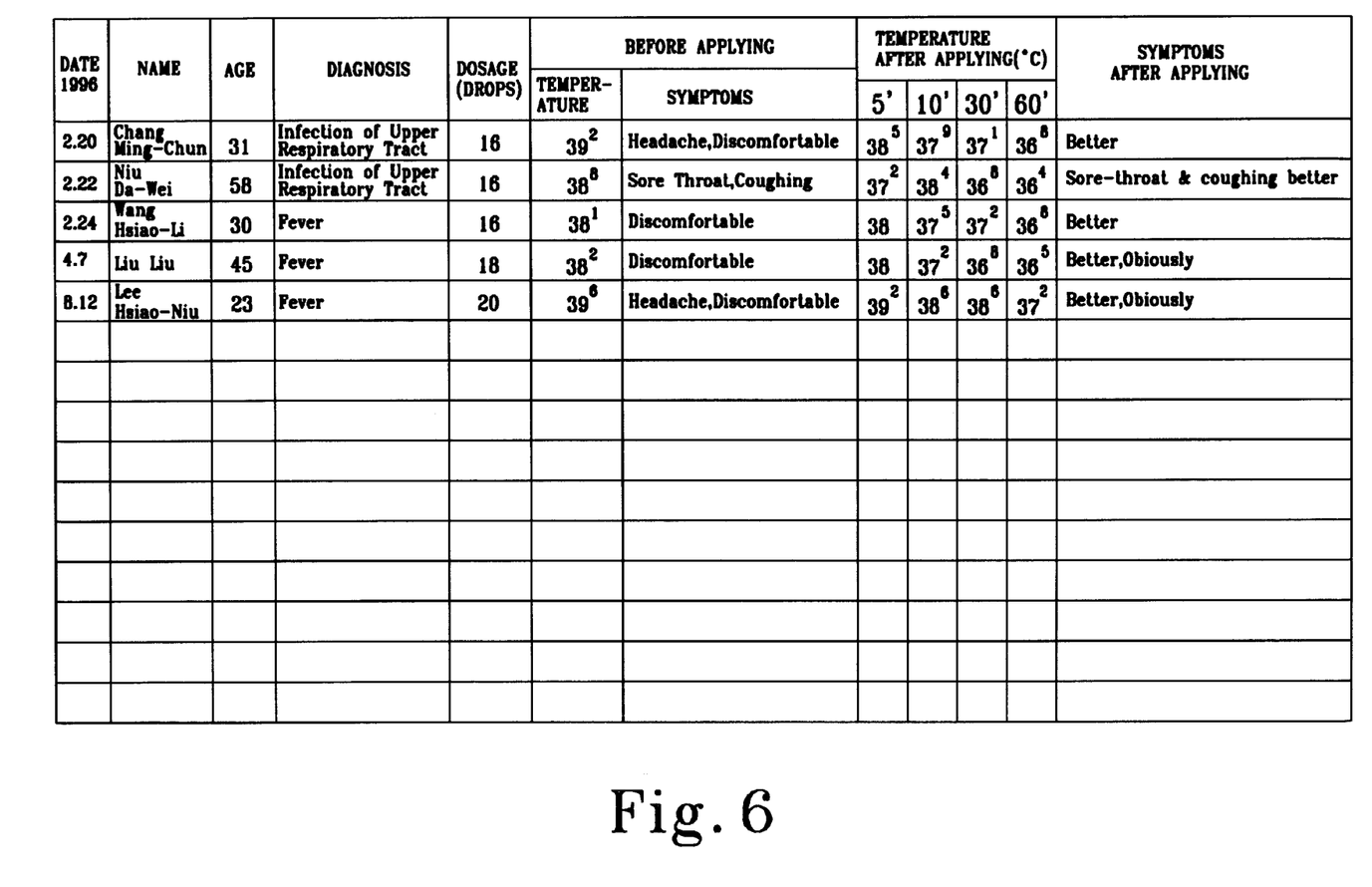

Experiment is started at room temperature within 20~25° C. Using male Wistar rats weighing 170~210 g for experiment. Basic body temperature is measured three times before experiment. Apply mingling ferment liquid for fresh beer to Wistar rats of body temperature variation $\leq 0.3°$ C. by hypodermic injection, then measure the temperature of the Wistar rats 4 hours after hypodermic injection, then select 50 Wistar rats from those rats whose body temperature rose over 1° C., and then divide the selected 50 Wistar rats into five groups, i.e., Nasal spray (drop) high dosage group, Nasal spray (drop) low dosage group, Analgin group, Tylenol P.O. Liquid group, and Blank reference group (See FIG. 2). Every experimental group include 10 Wistar rats. The Wistar rats of each experimental group receive respective medicine 0.14 ml/kg per dosage, which was given within 10 minutes, total ten dosages or 1.4 ml/kg. The Wistar rats of the Nasal spray (drop) high dosage group and the Wistar rats of the Nasal spray (drop) low dosage group receive Nasal spray (drop) of different concentrations, i.e., the high dosage group receives equivalent raw medicine 2.4 g/kg, and the low dosage group receives equivalent raw medicine 1.2 g/kg. Analgin is diluted and then applied to the Analgin group, and the accumulated amount of Analgin is 0.08 g/kg. Tylenol P.O. liquid is given to the Wistar rats of the Tylenol P.O. liquid group, and the total amount of the applied medicine is 0.14 g/kg. The Wistar rats of the Blank reference group receive physical saline solution of equal volume. The temperature of the Wistar rats is measured at 0.5, 1, 2, and 4 hours after the application of a medicine. The experimental results are shown in FIG. 2. In comparison with the Blank reference group, $*P<0.05$, $**P<0.01$.

The result of the experiment indicates that: in comparison with the Blank reference group, Nasal spray (drop), Analgin and Tylenol P.O. liquid achieve a fever relieving effect at different extent. Among the tested medicines, Analgin is less effective in fever relieving, and shows a prominent fever relieving effect ($P<0.05$) two hours after applying. Nasal spray (drop) high dosage and Tylenol P.O. liquid show a better fever relieving effect. In comparison with the Blank reference group, Nasal spray (drop) high dosage and Tylenol P.O. liquid show a prominent fever relieving effect at 0.5, 1, 2 and 4 hours after applying. From the whole fever relieving process, Tylenol P.O. liquid shows a better effect at the early stage, however the effective time of Nasal spray (drop) lasts longer than Tylenol P.O. liquid.

B. Toxicologic Research on Nasal Spray (Drop)

[Test Samples]

1. Nasal spray (drop) containing raw medicine 2 g or 4 g, clinical dosage for children 2 drops (about 0.1 ml) per every 10 kgs, dosage applied within 10 minutes, continuous dosage given for ten times, total amount of applied nasal spray (drop) about 0.2 g/kg.

2. Wistar rat, weighing from 180 g to 220 g supplied by Animal Experimental Center of Ho-Nan Medical University.

[Method and Result]

1. Acute toxin test

Healthy Wistar rats weighting from 180~220 g were selected, and randomly divided into three groups subject to their body weight and sex, namely, the Nasal spray (drop) high dosage group, the Nasal spray (drop) low dosage group, and the Blank reference group. Each group included 5 male rats and 5 female rats. The test was proceeded under room temperature within 20~25° C. The rats of the Nasal spray (drop) high dosage group received Nasal spray (drop) containing 4 g/ml raw medicine. The rats of the Nasal spray (drop) low dosage group received Nasal (drop) containing 2 g/ml raw medicine. The rates of the Blank reference group received saline solution 0.1 mg/kg per dosage per 10 minutes, total 10 dosages at an interval of 8 hours. The medicine application process was repeated to such an extent that the rats of the high dosage group received total equivalent to raw medicine 8 g/kg, the rats of the low dosage group received total equivalent to raw medicine 4 g/kg. Medicines were given under room temperature. An observation was continued for seven days to see the changes of the body weight and fur color of the rats, the activity, as well as water drinking and food eating conditions of the rats. After 7-day observation, a dissection of the rats showed no any abnormal change at the internal organs of heart, liver, spleen, lungs, kidneys, stomach, enteron, brain, nose, throat, trachea, and bronchi. The test shows that an application of 8 g/kg Nasal spray (drop) to rats does not cause an acute toxic reaction. The dosage used in the test is equivalent to 40 times of clinical dosage.

Nasal spray (drop) acute toxic test result

| Organ system | Reaction after Applying |
| --- | --- |
| central nervous system and body movement | normal, no abnormal reaction to stimulation |
| autonomic nerve system | pupil of the eye normal |
| respiratory system | breathing smooth, frequency and rhythm normal, no coughing, no asthma |
| heart blood-vascular system | heart beating normal |
| gastro-enteric system | stool in solid form, no abnormal indications |
| fur | bright color, good elasticity, no abnormal indications |

2. Irritation test 20 healthy rats weighing from 180~220 g were selected, and randomly divided into two groups, namely, the Nasal spray (drop) group and the Blank reference group. Each group included 5 female rats and 5 male rats. The test was proceeded at room temperature 22±2° C. Nasal spray (drop) was dropped into the nasal cavity once per 10 minutes at the dosage of 0.1 ml/kg. Total 10 dosages or 1 ml/kg (containing raw medicine 2 g) were given. After applying, the rats showed normal in breathing. Neither coughing nor asthma were found. A dissection was proceeded 24 hours after applying. The dissection showed no abnormal indications at the respiratory passage mucosa of the nose, throat, trachea, bronchi of the rats. The test shows that the application of Nasal spray (drop) does not cause an irritation.

As indicated above, Nasal spray (drop) achieves a satisfactory effect in fever relieving, and is better than Analgin or approximately equal to Tylenol P.O. liquid in effect. It is not irritate. 40 times over clinical dosage (8 g/kg raw medicine) shows no acute toxic reaction at rats. This test explains that Nasal spray (drop) is a safety medicine.

FIGS. from 3 through 6 show a medical effect survey report indicating the effect of Nasal spray (drop) in a clinical survey. From the report, it indicates that Nasal spray (drop) can be quickly absorbed by the nasal mucosa to control the condition of the patient within a short period of time after its application. Therefore, Nasal spray (drop) achieves significant medical effect.

As indicated above, the present invention provides a Nasal spray (drop) obtained from Bupleurum Scorzonerifolium Willd, *Radix lastidis* Indigotica, *Folium lastidis* and Vitamin C that can be directly applied to the nasal cavity and absorbed by the nasal mucosa to treat fever/cold.

What is claimed is:

1. A nasal spray (drop) for application to the nasal cavity for absorption by the nasal mucosa to treat fever/cold, comprising 250~300 g Bulpleurum Scorzonerifolium Willd, 120~144 g *Radix lastidis* Indigotica, 120~144 g *Folium lastidis*, and 10~12 g Vitamin C.

2. The nasal spray (drop) of claim 1 wherein said Bulpleurum Scorzonerifolium Willd comprises β-terpinene, camphene, β-fenchene, isoborneol, β-terpincol, α-copaene, α-farnesene, aromadendrene, β-elemene, γ-muurolene, patchoulane, and ledol.

3. The nasal spray (drop) of claim 2 wherein said Bulpleurum Scorzonerifolium Willd further comprises saikosaponin total 0.15% including saikosaponin a 0.05%, a minor amount of saikosaponin d and saikosaponin c 0.10%.

4. The nasal spray (drop) of claim 2 wherein said Bulpleurum Scorzonerifolium Willd further comprises progesterone compound.

5. The nasal spray (drop) of claim 4 wherein said progesterone compound comprises quercetin, isoquercetin, isorhamnetin, rutin, narcissin.

6. The nasal spray (drop) of claim 1 wherein said *Radix lastidis* Indigotica comprises indigotin, indigo, indirubin, β-sitosterol, γ-sitosterol, amino acids.

7. The nasal spray (drop) of claim 6 wherein said amino acids include arginine, glutamic acid, tyrosine, proline, valine, γ-aminobutyric acid.

8. The nasal spray (drop) of claim 6 wherein said *Radix lastidis* Indigotica further comprises sinigri-n, indoxyl-β-glucoside, tryptanthrine, thiocyano-2-hydroxy-3-butene, epigoitrin, adenosine, palmitic acid, sucrose, and protein polysaccarides comprising 12% amino acid.

9. The nasal spray (drop) of claim 1 wherein said *Folium lastidis* comprises indigo, indigotin, isatan B, and indirubin.

10. The nasal spray (drop) of claim 9 wherein said *Folium lastidis* further comprises inorganic elements including iron, titanium, manganese, zinc, copper, cobalt, nickel, selenium, chrome, and arsenic.

11. The nasal spray (drop) of claim 9 wherein said isatan B is turned into indigotin and D-xylo-5-hexulofuranosonic acid when dissolved in water.

12. The nasal spray (drop) of claim 1 wherein said Vitamin C is comprised of dextrose.

13. A method of preparing a nasal spray (drop) as claimed in claim 1, comprising the steps of (a) dipping Bupleurum Scorzonerifolium Willd in water, then boiling Bupleurum Scorzonerifolium Willd in water and distilling the steam so as to obtain a volatile oil and a Bupleurum Scorzonerifolium Willd filtrate, leaving a Bupleurum Scorzonerifolium Willd residue;

b) boiling *Radix lastidis* Indigotica and *Folium lastidis* in water, then filtering the boiled liquid to obtain a *Radix lastidis* Indigotica and *Folium lastidis* filtrate;

c) mixing the residue of Bupleurum Scorzonerifolium Willd obtained from step a) with the residue of *Radix lastidis* Indigotica and *Folium lastidis* obtained from step b) into a mixture, then boiling the mixture in water, then removing the liquid from the solid matter, and then boiling the liquid thus obtained in water, and then removing the solid matter from the liquid so as to obtain a filtrate;

d) mixing the Bulplerum Scorzonerifolium Willd filtrate obtained from step a) and the *Radix lastidis* Indigotica and *Folium lastidis* filtrate obtained from step b) with the filtrate obtained from step c) into a mixture, and then condensing the mixture, and then putting ethyl alcohol to the mixture so as to obtain a liquid;

e) standing the alcohol contained liquid thus obtained from step d) at room temperature for a number of hours, and then recycling ethyl alcohol from the liquid;

f) dissolving Vitamin C the volatile oil obtained from step a), then mixing the dissolved volatile oil and Vitamin C mixture with the liquid obtained from step e), then removing solid matter from the mixture so as to obtained finished nasal liquid, and then packing the finished nasal liquid in the individual containers.

14. The method of preparing a nasal spray (drop) according to claim 13, wherein during step a), Bupleurum Scorzonerifolium Willd is dipped in water at the ratio of one part of Bupleurum Scorzonerifolium Willd with one part of water for two hours, and then dipped Bupleurum Scorzonerifolium Willd is boiled in water at the ration of one part of Bupleurum Scorzonerifolium Willd with four parts of water during.

15. The method of preparing a nasal spray (drop) according to claim 13 wherein the amount of volatine obtained from step a) is about 2 ml~2.4 ml.

16. The method of preparing a nasal spray (drop) according to claim 13 wherein the amount of the Bupleurum Scorzonerifolium Willd filtrate obtained from step a) is about 1000 ml~1200 ml.

17. The method of preparing a nasal spray (drop) according to claim 13 wherein during step b), *Radix lastidis* Indigotica and *Folium lastidis* are boiled in water for one hour at the ratio of one part of *Radix lastidis* Indigotica, one part of *Folium lastidis* in water, and 14 parts of water.

18. The method of preparing a nasal spray (drop) according to claim 13 wherein during step c), the mixture of the residue of Bupleurum Scorzonerifolium Willd and the residue of *Radix lastidis* Indigotica and *Folium lastidis* is boiled in water for one hour at ration of one part of the mixture with 5 parts of water.

19. The method of preparing a nasal spray (drop) according to claim 13 wherein during step c), the mixture of the residue obtained from step a) and the residue obtained from step b) is boiled in water, then the boiled liquid is removed from the solid matter, and then boiled liquid is boiled in water again at the ration of one part of the boiled liquid with four parts of water.

20. The method of preparing a nasal spray (drop) according to claim 13, wherein during step e), the mixture of the filtrate obtained from step a), the filtrate obtained from step b) and the filtrate obtained from step c) is condensed to a 1 ml liquid containing to 1 g raw medicine.

21. The method of preparing a nasal spray (drop) according to claim 13, wherein during step e), 95% ethyl alcohol is put to the condensed liquid to reach 70% alcohol content.

22. The method of preparing a nasal spray (drop) according to claim 13, wherein the ethyl alcohol is recycled to such an extent that 1 ml liquid contains 1 g raw medicine.

* * * * *